(12) United States Patent
Helfenbein et al.

(10) Patent No.: US 7,771,544 B2
(45) Date of Patent: Aug. 10, 2010

(54) CLEANING OR CARE APPARATUS FOR MEDICAL OF DENTAL INSTRUMENTS

(75) Inventors: Gerald Helfenbein, Gilgenberg (AT); Daniel Schaffarzick, Elsbethen (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 938 days.

(21) Appl. No.: 11/581,901

(22) Filed: Oct. 16, 2006

(65) Prior Publication Data
US 2008/0012291 A1    Jan. 17, 2008

(30) Foreign Application Priority Data
Oct. 18, 2005    (EP)    ................... 05022643

(51) Int. Cl.
*B08B 3/04*    (2006.01)
(52) U.S. Cl. ............... 134/169 C; 134/170; 422/297; 422/300
(58) Field of Classification Search ............ 134/166 C, 134/169 C, 170, 171; 422/296, 297, 300; 285/91, 136.1; 137/614.03
See application file for complete search history.

(56) References Cited

U.S. PATENT DOCUMENTS

| | | | | |
|---|---|---|---|---|
| 2,884,981 A | * | 5/1959 | Wurzburger | ................. 411/143 |
| 5,269,030 A | * | 12/1993 | Pahno et al. | .................... 5/604 |
| 5,343,855 A | * | 9/1994 | Iida et al. | ..................... 600/157 |
| 5,380,369 A | * | 1/1995 | Steinhauser et al. | ............ 134/1 |
| 5,533,539 A | * | 7/1996 | Sutter et al. | ................. 134/95.2 |
| 5,723,090 A | | 3/1998 | Beerstecher et al. | |
| 5,749,385 A | * | 5/1998 | Rochette et al. | ............. 134/199 |
| 5,845,943 A | * | 12/1998 | Ramacier et al. | .............. 285/12 |
| 5,993,754 A | * | 11/1999 | Lemmen et al. | ............. 422/293 |
| 6,007,686 A | | 12/1999 | Welch et al. | |
| 7,377,555 B2 | * | 5/2008 | Smith, III | .................... 285/317 |

FOREIGN PATENT DOCUMENTS

| | | |
|---|---|---|
| AT | 400 105 | 10/1995 |
| DE | 31 17 264105 | 11/1982 |
| DE | 199 13 943105 | 9/2000 |
| EP | 0 732 083105 | 9/1996 |
| JP | 07-269761 | * 10/1995 |

OTHER PUBLICATIONS

European Search Report for EP 05 02 2643.

* cited by examiner

*Primary Examiner*—Frankie L Stinson
(74) *Attorney, Agent, or Firm*—Klarquist Sparkman, LLP

(57) ABSTRACT

A connecting device of a cleaning or care apparatus or a cleaning cassette comprises a blocking device which is movable between a first position and a second position and prevents loosening or displacement of an instrument that is to be cleaned during a cleaning or care operation because of the pressure exerted by the cleaning or care media. In some embodiments, a direct or indirect operative connection between the blocking device and a component of the cleaning or care apparatus or between the blocking device and at least a part of the cassette is provided, which transmits to the blocking device the force required to move the blocking device from the first position into the second position. In other embodiments, the blocking device is moved from the first position into the second position by the action of the media in the line, e.g., either by direct contact with the media or indirectly through contact with another intermediate element.

13 Claims, 5 Drawing Sheets

CLEANING OR CARE APPARATUS FOR MEDICAL OF DENTAL INSTRUMENTS

CROSS REFERENCE TO RELATED APPLICATION

The present application claims priority from pending European Patent Application No. 05022643.0, filed Oct. 18, 2005, which is incorporated herein by reference.

BACKGROUND

1. Field

The present invention relates to a cleaning or care apparatus for medical and dental instruments, in particular the connecting device of a cleaning or care apparatus or a cleaning cassette of a cleaning or care apparatus.

2. Description of Prior Art

Such an apparatus is known from the Austrian patent AT 400 105 B. For connecting a medical instrument that is to be cleaned, one or more connecting devices to which the instrument is attached by plug or push connection are provided on the apparatus. As an alternative, an instrument to be cleaned may also be attached to a connecting device of a cleaning cassette as disclosed in the German application DE 31 17 264. The cleaning cassette is then inserted into the cleaning or care apparatus. The connecting devices for the cleaning or care apparatus or the cleaning cassette are connected and/or connectable to one or more sources of media and carry the media through the interior into the instrument to be cleaned. The media, e.g., compressed air, cleaning agent, disinfectant or lubricant, are then conveyed under pressure into the instruments to be cleaned. It is therefore necessary to take measures to ensure that an instrument to be cleaned is not displaced from the connecting device due to the pressure during a cleaning or care process, so that leakage occurs in the area of transfer of the media into the instruments and at least some media escapes or the instrument is not disengaged entirely from the connecting device.

Various measures for securely attaching the instrument attached to the connecting device are known from the state of the art. With a known cleaning cassette, the connecting device is designed so that the frictional resistance between the connecting device and the attached instrument is high enough so that the instrument is not detached by the pressure. However, this also increases the force required for attaching the instrument to the connecting device and for releasing the instrument from the connecting device in a manner which is a disadvantage, so that such a connecting device is difficult for the user to operate.

Known cleaning and care apparatuses having connecting devices for an instrument that is to be cleaned include blocking mechanisms to be operated by the user. An exemplary embodiment of such a blocking mechanism is illustrated as an example in FIG. 1 as part of a known connecting device 100. The connecting device 100 comprises a plug pin 101 to which an instrument that is to be cleaned is attached by pushing it onto the pin and/or connected by plug, a flange 102 and a blocking mechanism 103. One or more media are supplied to the connecting device 100 through a line 108. The blocking mechanism 103 consists of a blocking element 104 with a nose 105, a pin 106 and a pushbutton 107. Pin 106 is accommodated in a bore in the flange 102 and is prestressed by a spring which is also arranged in the flange 102. Blocking element 104 is accommodated in a groove in the pin connector 101 and is connected to the pin 106. If an instrument is attached to the pin connector 101, a shoulder of the coupling pipe of the instrument is pushed over the nose 105 and presses the nose 105 and the blocking element 104 into the groove. As soon as the shoulder has slipped over the nose 105, the nose 105 returns to its original position, as illustrated in FIG. 1, where it protrudes above the surface of the pin connector 101 and engages behind the shoulder of the instrument so that the instrument is secured on the connecting device. To release the instrument, the user must depress the pushbutton 107 against the spring force (toward the bottom in FIG. 1), so that the blocking element 104 and nose 105 are moved into the groove and the instrument can be pulled away from the pin connector as long as the pushbutton 107 remains depressed.

One disadvantage of this type of blocking mechanism is that it must be operated by the user, but it is often difficult to gain access to the pushbutton and in most cases one must use two hands to operate the pushbutton while removing the instrument at the same time.

Therefore, the object of the present invention is to create a connecting device to which the instruments can be reliably attached so that they are not pushed or released due to the media under pressure during the cleaning or care process and an uncomplicated attachment and release of the instruments for the user is allowed.

SUMMARY

Described below are embodiments of a connecting device that addresses problems of conventional approaches.

According to some embodiments, a connecting device is arranged at least partially in a cleaning or care apparatus or in a cassette, and comprises a direct or indirect operative connection between the blocking device and a component of the cleaning or care apparatus, or between the blocking device and at least a part of the cassette, the connection transmitting to the blocking device the force required to move the blocking device from the first position into the second position.

The operative connection may be designed as an operative connection which exists continuously or is built up. An operative connection may be established, for example, during an action which is associated with the cleaning or care process or preparations for this process, in particular during the loading of the connecting device or the cleaning cassette with the instruments or during the insertion of the cleaning cassette into the cleaning or care apparatus. As a result of this action, there is a relative movement and thus an approach of the component of the cleaning or care apparatus or a part of the cassette and the connecting device and as a result of this approach the operative connection is built up. The relative movement between a component of the cleaning or care apparatus or a part of the cassette and the connecting device may take place here as a translational and/or rotational movement.

The operative connection may be designed as a non-contacting, preferably magnetic operative connection in which at least parts of the blocking device and the component of the cleaning or care apparatus or the cassette are magnetic or may be designed as a contacting operative connection in which the component of the cleaning or care apparatus or a part of the cassette comes in contact with the blocking device.

According to other embodiments, a connecting bore between the blocking device and the media bore allows a part of the medium which is under pressure and flowing in the media bore to be drained to the blocking device. The medium also moves the blocking device from the first position into the second position indirectly, e.g., by displacement of a shift element arranged in a bore or directly, e.g., by deformation of an elastically deformable element.

Suitable instruments with which the connecting device can be used include, but are not limited to, handpieces and contra-angle handpieces for driving a wide variety of tools such as rotary drills, files, tools for removing dental calculus, saws, etc., function handpieces for dispensing water or air and non-motorized manual instruments, such as medical mirrors, probes and the like.

The foregoing and other features and advantages will become more apparent from the following detailed description and with reference to the accompanying drawings:

DETAILED DESCRIPTION

Figure 1:
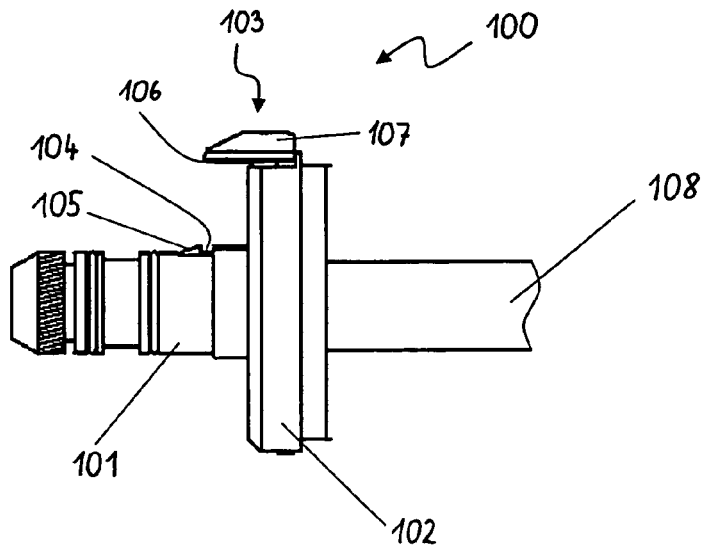
FIG. 1 shows a connecting device known from the state of the art having a blocking mechanism for attaching the instrument.
Figure 2:
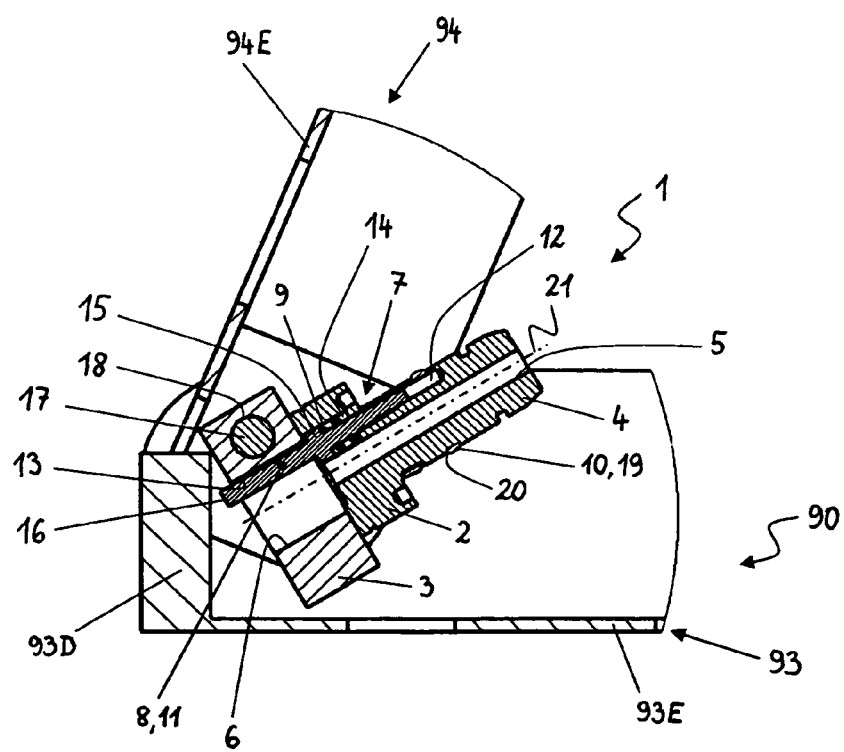
FIG. 2 shows a first embodiment of a connecting device, whereby the connecting device is arranged rotatably in a cleaning cassette and the blocking device for the instrument is moved by the cassette.
Figure 10:
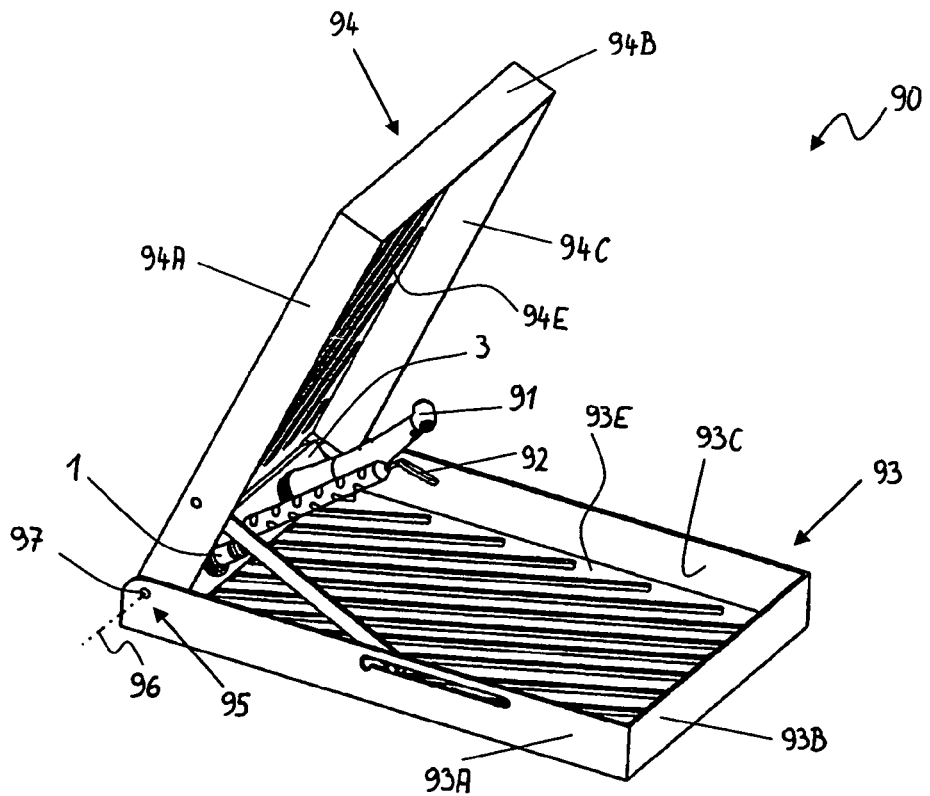
FIG. 10 shows a cleaning cassette with an inventive connecting device.

The connecting device 1 shown in FIG. 2 resembles in its design a standardized motor attachment. It comprises a stop 2 which limits the depth of insertion of the plug pin 4 of an instrument to be connected to the connecting device 1, e.g., a handpiece 91 or a mirror 92 (FIG. 10). The stop 2 is attached to a carrier 3 of a cassette 90, with several identical or different connecting devices 1 preferably being arranged on the carrier 3 in a known way. The plug pin 4 has the same cylindrical shape and the same dimensions as a standardized coupling pin of a motor for driving an instrument.

A central media bore or media line 5 passes through connecting device 1, connecting a source of a cleaning medium or care medium to the interior of the instrument that is plugged to or pushed onto the connection. Other lines and/or bores may of course also be provided so that the instrument can be cleaned or cared for using more than one medium. Media line 5 is continued in a bore or line 6 through the carrier 3. If the cleaning cassette 90 is inserted into a cleaning or care apparatus, the lines 5, 6 are connected to the sources of the media via a coupling in the cleaning or care apparatus and via media lines.

Connecting device 1 also includes a blocking device 7 with a shift element 8, a spring element 9 and a blocking element 10. Shift element 8 is designed as a pin 11 which is held so that it is movable, in particular being displaceable, in a bore 12 in the connecting device 1 and in a bore 13 in the carrier 3. Pin 11 is under prestress by spring element 9 in the form of a spiral spring. Spring element 9 is held in a chamber 14, the diameter of which is greater than the diameter of the bore 12, and it pressed the flange 15 of the pin 11 against the side wall of the chamber 14 and/or the carrier 3. The length of the pin 11 is such that in this relaxed state of the spring element 9, the end 16 of the pin 11 protrudes out of the bore 12 and/or 13.

Blocking element 10 in the form of a spring ring 19 is arranged in a ring groove 20 in the plug pin 4. A through-cut in the ring groove 20 connects the ring groove 20 to the bore 12 arranged beneath it.

Connecting device 1 is mounted so that it is movable, i.e., rotatable or pivotable, about the transverse axis 17. Transverse axis 17 is held in a bore 18 in the carrier 3; however, the transverse axis may of course also be held in a bore in the connecting device 1.

Figure 4:
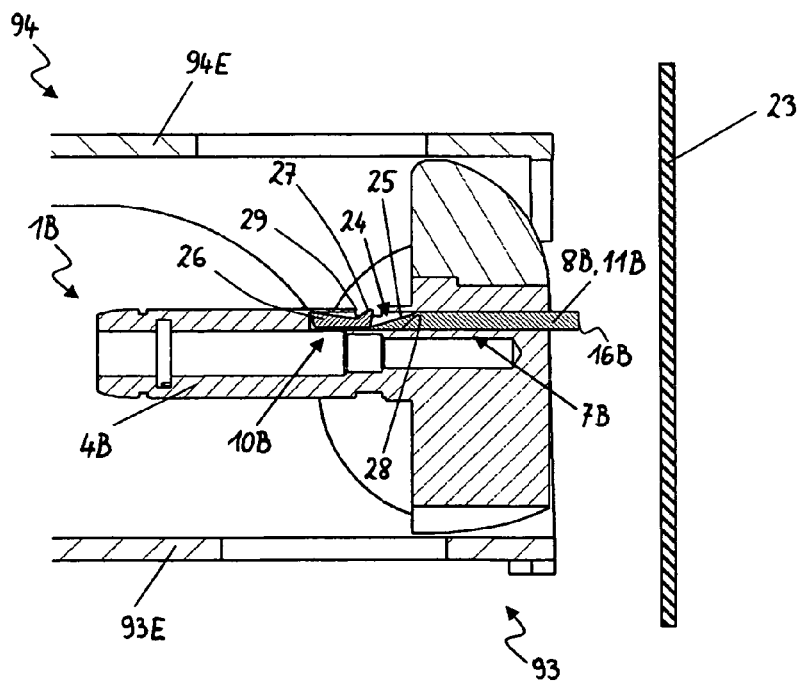
FIG. 4 shows a third embodiment of a connecting device with which the blocking device comprises an inclined plane and a projection.

As shown in FIG. 10 in particular, the cassette 90 consists of a base part 93 and a cover 94, which are rotatably and/or pivotably connected to one another by a hinge 95. The base part 93 and cover 94 are rectangular, with the dimensions of the cover 94 being somewhat smaller than those of the base part 93 so that in the closed collapsed state, the cover 94 is accommodated in the base part 93. Base part 93 and cover 94 each have three side walls 93A, 93B, 93C and 94A, 94B, 94C. The bottom surface 93A and cover surface 94A are each cut so that the cleaning media or care media can run out of the cassette 90 after passing through the instruments 91, 92 and/ or after the outside cleaning. The cassette 90 holds carrier 3 with three connecting devices 1. To ensure easy connection of connecting device 1 to the coupling in the cleaning or care apparatus, the fourth side wall (rear wall) is omitted completely (as illustrated in FIG. 4) or it is provided with passages for the couplings. The rear wall may be designed as part of the cover 94 or as shown in FIG. 2 it may be designed as part of the base part 93 and then labeled accordingly with reference numeral 93D.

If the connecting device 1 is pivoted out of the position illustrated in FIG. 2, pivoting it about the transverse axis 17 in the direction of the rear wall 93D, then the blocking device 7 and the shift element 8 move along with the connecting device 1 in the first part of the relative movement until the end 16 of the shift element 8 comes in contact with the side of the rear wall 93D facing the connecting device 1. This forms a contacting operative connection in the sense of a mechanical coupling and in the form of direct contact between the blocking device 7 and the rear wall 93D as part of the cassette 90. If the connecting device 1 is pivoted further in the direction of the rear wall 93D, then the operative connection transmits the force required to move the blocking device 7 from the first position into the second position, transferring the force to the shift element 8 via the rear wall 93D, so that the shift element 8 leaves its position illustrated in FIG. 2 and is displaced against the force of the spring element 9 in relation to the connecting device 1 in the direction of the spring ring 19 until reaching the through-cut between the bore 12 and the ring groove 20.

In its basic position, the spring ring 19, arranged in the ring groove 20, protrudes into the through-cut and into the bore 20 and does not protrude beyond the outer lateral surface of the plug pin 4. In this position, an instrument 91, 92 can be connected to or pushed onto the connecting device or can be released from the connecting device. When the shift element 8 is displaced beneath the through-cut, it displaces the spring ring 19 radially outward—in relation to the longitudinal axis 21 of the plug pin 4—so that the spring ring 19 protrudes beyond the outer lateral surface of the plug pin 4. If an instrument 91, 92 is attached to the plug pin 4, the spring ring 19 presses against a component of the instrument 91, 92 against the coupling pipe in particular, so that the instrument 91, 92 is secured against displacement or loosening.

To be able to remove the instrument 91, 92 from the plug pin 4 again, e.g., after conclusion of the cleaning or care cycle, the spring ring 19 must be returned to its original position. This is done by pivoting the connecting device 1 away from the rear wall 93D about the transverse axis 17, thus eliminating the contacting operative connection between the blocking device 7, i.e., shift element 8, and the rear wall 93D. The spring element 9, which is put under tension by the previous displacement of shift element 8, thus has an opportunity to relax, so that the shift element 8 is displaced in the direction of the rear wall 93D by way of the flange 15 which is contacted by the spring element 9, and resumes the position illustrated in FIG. 2. In this position, the shift element 8 is no longer arranged beneath the through-cut, so that the spring ring 19 again returns into the through-cut and the bore 12 and no longer protrudes beyond the outer lateral surface of the plug pin 4.

The exemplary embodiment depicted in FIG. 2, in which the connecting device 1 is rotatably arranged on a transverse axis 17, can be implemented accordingly in a cleaning or care apparatus instead of in a cleaning cassette 90. In this case, the rear wall 93D is replaced by a component of the cleaning or care apparatus, in particular by the rear wall of the interior of the cleaning or care apparatus.

In another exemplary embodiment not shown in the figure, the connecting device 1 has the same design as in FIG. 2 but is arranged so that it is rotatable about the longitudinal axis, whereby any longitudinal axis, e.g., central axis 21 of the connecting device 1 can be selected, but it need not be identical to the longitudinal axis of the shift element 8. The connecting device 1 is arranged on a wall, preferably the rear wall of the interior of the cleaning or care apparatus. If the connecting device 1 rotates about the longitudinal axis 21 and thus rotates in relation to the rear wall, the shift element 8 travels along a circular or arc-shaped path. Along this path, the wall has a varying wall thickness which is formed, for example, by a deepening groove or by an inclined plane. If the shift element 8 which is under pretension due to a spring element 9 is situated at the location of the lowest wall thickness, then it protrudes at its end 16 into the groove and assumes a position like that illustrated in FIG. 2 so that an instrument can be pushed onto the connecting device 1 or can be released from the connecting device 1. If the connecting device 1 rotates about the longitudinal axis, then the shift element 8 is pressed by the increasing wall thickness against the spring force of the spring element 9 into the bore 12 of the connecting device 1 in which it cooperates with the blocking element 10 as illustrated and described in conjunction with FIG. 2 to secure the instrument 91, 92 on the connecting device 1. To release the instruments 91, 92 the connecting device 1 is rotated so that the shift element 8 is again situated at a location having a small wall thickness.

The advantage of this embodiment is in particular that very little space is needed for the relative movement between the connecting device 1 and the wall of the cleaning or care apparatus or, if the longitudinal axis is the same as the central axis 21 of the connecting device 1, then no movement space is needed. This is an advantage, in particular in cleaning and care apparatuses, where the available interior space is often limited. The rotational movement of the connecting device 1 may be accomplished either manually by the user or by means of force transmitting members such as gear wheels, belt drives or lever arms. In the latter case, the force transmitting member is connected to an operating element, the operating element preferably being formed by the door of the cleaning and care apparatus so that when the door is closed the instruments 91, 92 that are attached to the connecting device 1 are automatically secured and when the door is opened the instruments 91, 92 are automatically released and/or instruments 91, 92 can be attached to the connecting device 1.

Figure 3:
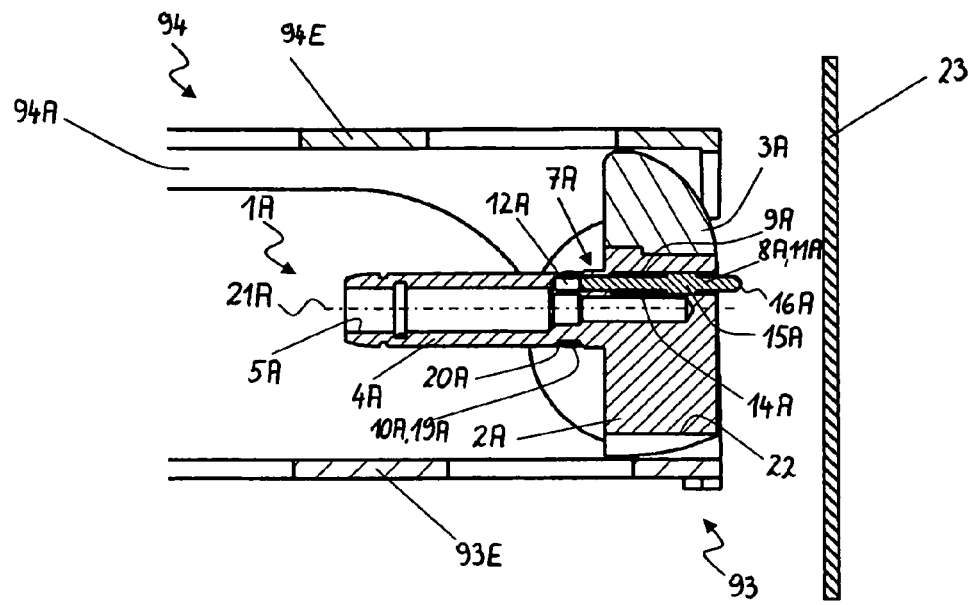
FIG. 3 shows a second embodiment of a connecting device with which the operative connection exists between the blocking device and the wall of the cleaning or care apparatus.

The connecting device 1A shown in FIG. 3 corresponds in its design and operation to the connecting device 1 from FIG. 2. It also includes a plug pin 4A with a media line 5A and a stop 2A. The carrier 3A is designed in the form of a strip and includes one or more bores 22 to receive one or more connecting devices 1A. The carrier 3A and connecting device 1A may be fixedly or rotatably (as shown in FIG. 10) arranged in the cleaning cassette 90, whereby the rotatability in the exemplary embodiment according to FIG. 3 is not a prerequisite for the function of the blocking device 7A. A rotatable carrier 3A and a rotatable connecting device 1A, however, mean a much more convenient option of attaching or releasing the instruments 91, 92 on the connecting device 1 or 1A for the user. If the carriers 3, 3A and/or connecting device 1, 1A are rotatably arranged in a cleaning cassette 90, then it is advantageous for the purpose of simple design if carriers 3, 3A and/or connecting device 1, 1A and cover 94 have a common axis of rotation 96, preferably formed by a single shaft 97.

The blocking device 7A comprises a shift element 8A in the form of a piston 11A having a flange 15A, a bore 12A to receive the shift element 8A, a spring element 9A accommodated in a chamber 14A and a spring ring 19A which is arranged in a ring groove 20A and serves as a blocking element 10A. The instrument 91, 92 is blocked and unlocked by shifting the shift element 8A and the spring ring 19A as described in conjunction with FIG. 2.

In contrast with the exemplary embodiment in FIG. 2, the shift element 8A of the connecting device 1A is shifted by a component of the cleaning or care apparatus, in particular through the rear wall 23 of the interior space of the cleaning or care apparatus into which the cleaning cassette 90 is inserted. While the cassette 90 is in use, the cassette approaches the component, i.e., the rear wall 23 until the end 16A of the piston 11A comes in contact with the rear wall 23 which in turn results in a contacting operative connection in the sense of a mechanical coupling. With a further approach to the rear wall 23, the operative connection transmits the force required for displacement to the shift element 8A so that the latter is shifted until it punctures up to the through-cut between the bore 12A and the ring groove 20A. When the cassette 90 is removed from the rear wall 23 and the operative connection is thus interrupted, the spring element 9A forces the shift element 8A back into the starting position illustrated in FIG. 3.

The exemplary embodiment of the connecting device 11B illustrated in FIG. 4 is largely identical in design and function to the connecting device 1A from FIG. 3. Here again, the locking of the instrument 91, 92 is accomplished through a contacting operative connection between a component of the cleaning or care apparatus, in particular the rear wall 23 of the interior of the cleaning or care apparatus, and the end 16B of the shift element 8B designed as a pin 11B.

In contrast with the connecting device 1A from FIG. 3, the end 24 of the shift element 8B opposite the end 16B is designed as an inclined plane 25. The blocking element 10B comprises a carrier 26 with a protrusion 27, preferably designed as a wedge-shaped protrusion, which facilitates the attachment of the instrument 91, 92 to the plug pin 4B. The carrier 26 and the shift element 8B are held in a common bore 28 which opens through an opening 29 in the jacket of the plug pin 4B.

When the end 16B of the pin 11B comes in contact with the wall 23, the pin 11B is shifted in the direction of the carrier 26, whereby the inclined plane 25 migrates below the carrier 26 and displaces it. The protrusion 27 is moved radially through the opening 29 and extends beyond the jacket of the plug pin 4B so that an instrument 91, 92 attached to the plug pin 4B and is secured there. To release the instrument 91, 92, the operative connection between the wall 23 and the shift element 8B is interrupted so that the shift element 8B and the protrusion 27 return to their position illustrated in FIG. 4. Preferably one or more spring elements are connected to the carrier 26 and/or the shift element 8B, relaxing after the operative connection is interrupted, in accordance with the spring elements 9, 9A of FIGS. 2 and 3, thereby producing or supporting the return movement of the shift element 8B and the protrusion 27.

Figure 5:
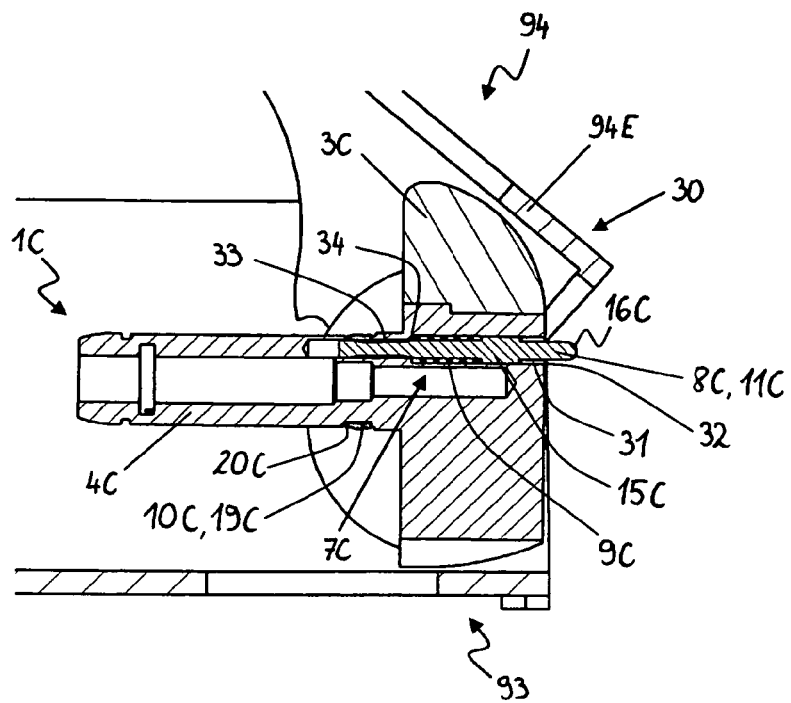
FIG. 5 shows a fourth embodiment of a connecting device with which the blocking device comprises a recess and a spring ring in a position in which the instrument is secured on the connecting device.
Figure 6:
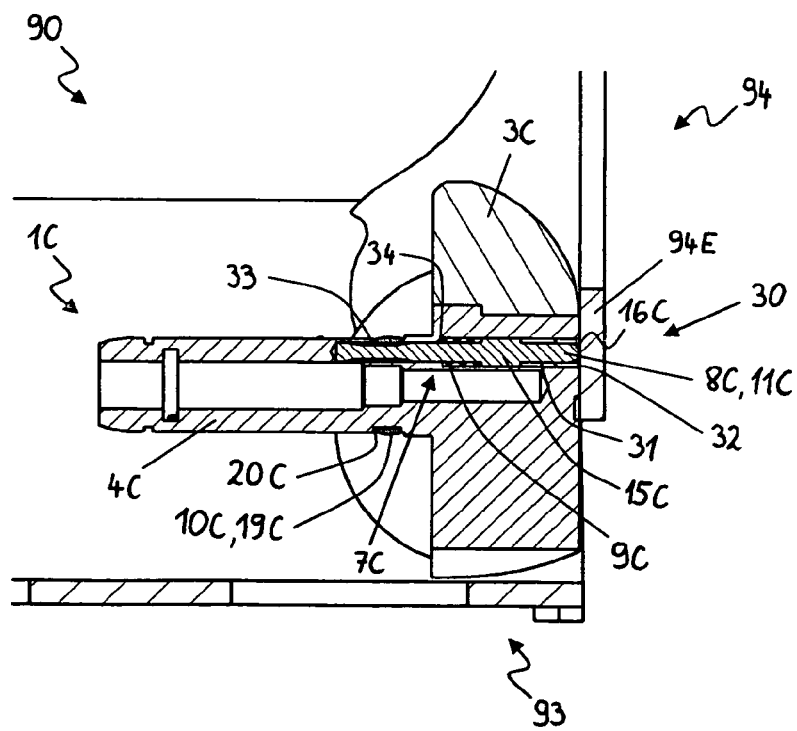
FIG. 6 shows the connecting device from FIG. 5 in a position in which the instrument can be pushed onto or plugged to the connecting device or can be released from the connecting device.

FIGS. 5 and 6 show a blocking device 7C of a connecting device 1C which is operated via the cover 94 of the cassette 90. To this end, the cover 94 has an engaging element 30 by which a contacting operative connection with the shift element 8C in the form of a piston 11C is established. Engaging element 30 can be a part of the cover surface 94E as shown, or any other suitable surface or member configured to contact the shift element. The advantage of this blocking device 7C is that the instruments 91, 92 are already secured when the cover 94 is closed as the conclusion of the operation of loading the cleaning cassette 90 and therefore shifting of the instruments 91, 92 during the insertion of the cassette 90 into the cleaning or care apparatus is also prevented.

FIG. 6 shows the cleaning cassette 90 with the cover 94 opened. A bore 31 passes through the connecting device 1C and ends in an opening 32 on the side of the connecting device 1C opposite the plug pin 4C. The blocking element 10C is designed as a spring ring 19C and is held in a ring groove 20C as described in conjunction with FIG. 2. Bore 31 and ring groove 20C are in turn interconnected by a through cut. The piston 11C is held movably in the bore 31. The piston 11C comprises a recess 33, the diameter of which is smaller than the diameter of the rest of the piston 11C.

In the position of the blocking device 7C shown in FIG. 6, the shift element 8C is completely inserted into the bore 31 due to the contacting operative connection between the end 16C and the engaging element 30. In this position, the recess 33 is in the area of the through-cut between the ring groove 20C and the bore 31 so that spring ring 19C protrudes into the through-cut and the recess 33, and does not protrude beyond the lateral surface of the plug pin 4C in particular. In this position, instrument 91, 92 can be attached to or removed from the plug pin 4C.

Bore 31 comprises a first and second section having different diameters, so that a shoulder 34 is formed where these two sections abut. Shoulder 34 serves as a support for a spring element 9C. Like spring element 9 of the connecting device 1 in FIG. 2, the second end of the spring element 9C is in contact with a flange 15C so that the spring element 9C is compressed by displacement of the shift element 8C. If the cover 94 is rotated about axis of rotation 96, as illustrated in FIG. 5, and thus the operative connection between the end 16C of the shift element 8C and the engaging element 30 is canceled, then the shift element 8C is shifted by the spring force of the relaxing spring element 9C in the direction of the opening 32. Therefore the section of the shift element 8C with the recess 33 is removed from the through-cut between the ring groove 20C and the bore 31 and a section of the shift element 8C having a larger diameter than the recess 33 reaches the through-cut. The section with the larger diameter displaces the spring ring radially outward so that it protrudes beyond the outer lateral surface of the plug pin 4C and secures an instrument 91, 92 that is attached to the plug pin 4C.

If, as described already in conjunction with FIG. 2, the connecting device 1 or 1C and/or the carrier 3 or 3C are designed to be rotatable or pivotable, then the engaging element 30 may also be used for transmitting the rotational movement of the cover 94 to the connecting device 1, 1C and/or the carrier 3, 3C. If the user turns the cover 94 further according to the direction of rotation illustrated in FIGS. 5 and 6, the engaging element 30 causes the connecting device 1 and/or the carrier 3 to rotate about the axis of rotation 96 so that the connecting device 1 or 1C assumes the position illustrated in FIG. 10 in which the plug pin 4, 4C points away from the base part 93. This makes it easier for the user to attach or release the instruments 91, 92.

Figure 7:
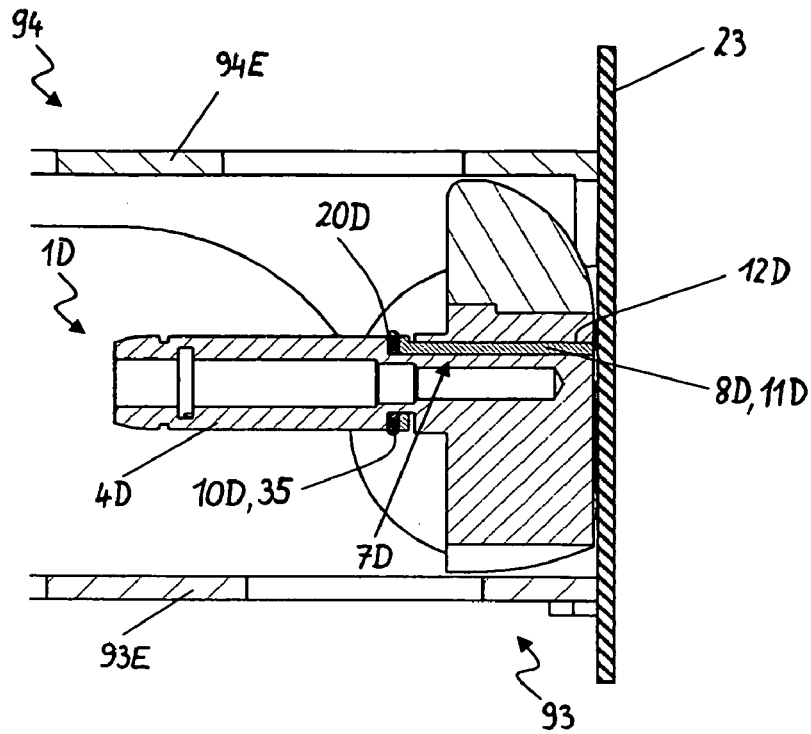
FIG. 7 shows a fifth embodiment of a connecting device with which the blocking device comprises an elastically deformable element in a position in which the instrument is secured on the connecting device.
Figure 8:
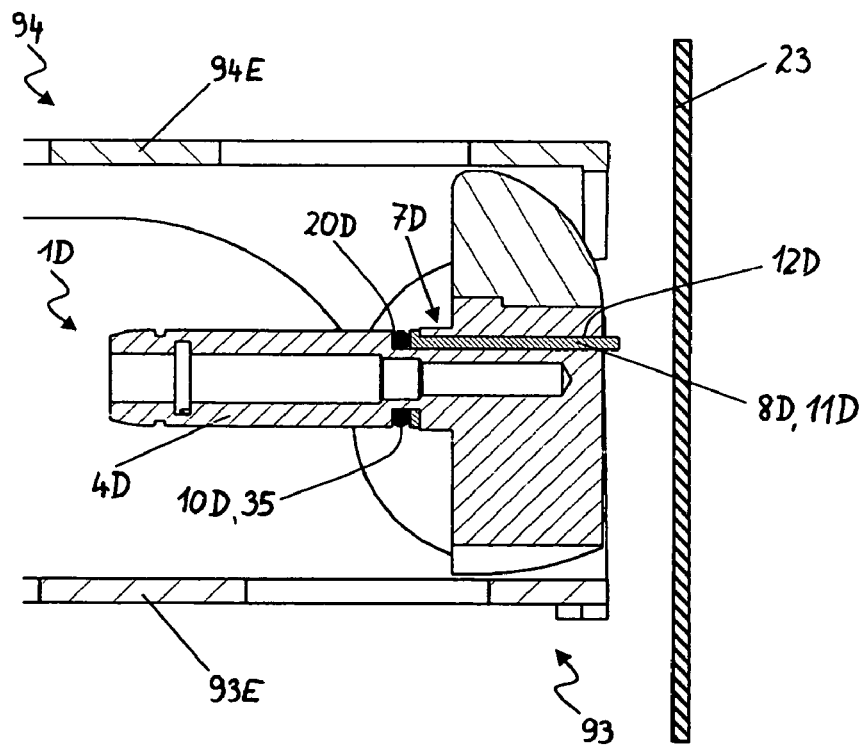
FIG. 8 shows the connecting device from FIG. 7 in a position in which the instrument can be pushed onto or plugged to the connecting device or can be released from the connecting device.

The blocking device 7D of a connecting device ID illustrated in FIGS. 7 and 8 comprises a shift element 8D in the form of a pin 11D which is held in a bore 12D and, together with a component of the cleaning or care apparatus, in particular the rear wall 23 of the interior of the cleaning or care apparatus into which the cleaning cassette 90 is inserted, forms a contacting operative connection, as already described in conjunction with FIG. 3. The force transmitted by the operative connection moves the shift element 8D from a first position into a second position. The advantage of the blocking device 7D lies in particular in its simple design.

FIG. 8 shows the position in which an instrument 91, 92 can be attached to the connecting device ID or released from the connecting device ID. The bore 12D ends in a ring groove 20D in which the blocking element 10D is held. The blocking element 10D is designed as an elastically deformable element 35, e.g., as an O-ring which does not protrude in this position beyond the outer lateral surface of the plug pin 4D.

If as illustrated in FIG. 7, the shift element 8D is moved by the wall 23 into the position in which an instrument 91, 92 attached to the plug pin 4D is secured, then the shift element 8D deforms the elastically deformable element 35 in such a way that it protrudes beyond the outer lateral surface of the plug pin 4D. For an improved uniform transmission of force, the shift element 8D has a flange-like broadened area arranged in the ring groove 20D on its end facing the elastically deformable element 35.

The reverse movement of the shift element 8D after the end of the contacting operative connection between the wall 23 and the shift element 8D is preferably accomplished solely by the restoring force of the elastically deformable element 35 which returns to its original shape and position as illustrated in FIG. 8 but may additionally also be supported by a spring element that is connected to the shift element 8D.

Figure 9:
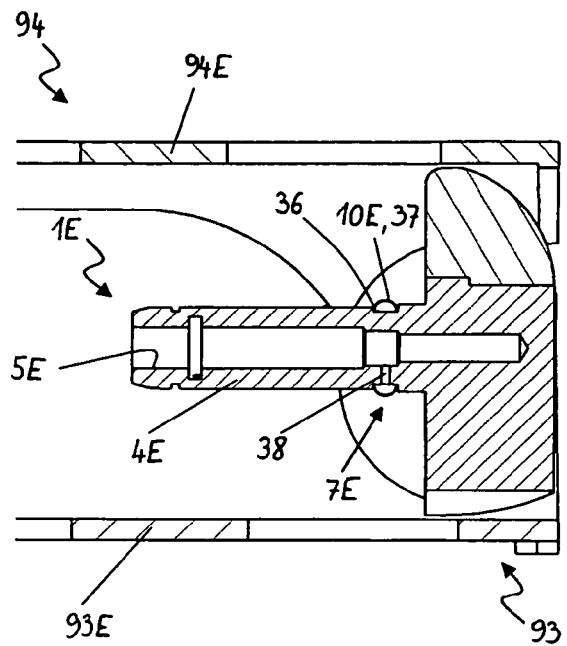
FIG. 9 shows a sixth embodiment of a connecting device with which the blocking device is connected to a media bore via a connecting bore.

The blocking device 7E according to FIG. 9 comprises a ring groove 36, in which is arranged a blocking element 10E which is designed as an elastically deformable element 37, e.g., a membrane. A connecting bore 38 between the blocking device 7E and the media bore or media line 5E allows some of the medium flowing in the media line 5E to flow out toward the blocking device 7E. The medium which is under pressure may be, for example, compressed air, water, a lubricant or a cleaning or care solution which flows through the connecting bore 38 into the ring groove 36 and deforms or expands the elastically deformable element 37 so that the elastically deformable element 37 protrudes beyond the outer lateral surface of the plug pin 4E. Therefore, the force required for the movement of the blocking device 7E from the first position into the second position is transferred directly to the blocking device 7E by the medium. The blocking device 7E thus assumes the position in which an instrument 91, 92 attached to the plug pin 7E is secured.

If the conveyance of the medium through the media line 5E is terminated, the flow of the medium into the ring groove 36 is also interrupted and the pressure exerted on the medium stops. Therefore the elastically deformable element 37 may return to its original undeformed or unstretched position in which it does not protrude beyond the outer lateral surface of the plug pin 4E. In this position an instrument 91, 92 may be attached to the plug pin 4E or removed from it.

There is, of course, also the possibility of preventing direct contact between the medium and the blocking element 10E, e.g., when there is a risk that the medium might attack or corrode the blocking element 10E. In this case, a shift element, preferably a pin, is displaceably mounted in the connecting bore 38 or another bore. The medium which flows out to the blocking device penetrates into the connecting bore 38 and displaces the shift element from a first position into a second position. The blocking device also comprises a blocking element 10E, which is preferably designed as a spring ring, a protrusion or an elastically deformable element and is shifted, displaced or deformed by the shift element in a manner similar to that described in conjunction with FIGS. 2 through 8, so that it protrudes beyond the outer lateral surface of the plug pin 4E. The transfer of force through the medium to the blocking element 10E of the blocking device 7E is thus accomplished indirectly.

The advantage of these two embodiments of the blocking device 7E is that a locking of the instrument 91, 92 is ensured in particular when pressure is exerted on the instrument 91, 92 by the media guidance.

In another exemplary embodiment, not illustrated in a figure here, the operative connection is designed as a noncontacting operative connection, preferably magnetic. The force required to move the blocking device from its first position to its second position is provided here by magnetic forces of attraction or repulsion. To do so, a part of the cleaning or care apparatus or a part of the cassette 90 and at least a part of the blocking device are magnetized, magnetizable or equipped with a permanent magnet. The magnetic components and/or permanent magnets begin to interact due to the approach of the component of the cleaning or care apparatus or the cassette 90 to the blocking device. This may be accomplished for example through an arrangement according to FIG. 3, whereby a magnetic wall 23 and a magnetic shift element 8A are provided. The poles of the magnetic wall 23 and the magnetic shift element 8A are arranged in such a way that the same poles face one another so that in the approach of the cassette to the wall 23 a repulsive effect occurs then, so that as already described in conjunction with FIG. 3, the shift element 8A is moved in the direction of the blocking element 10A. Clearly with a noncontacting operative connection, it is not necessary for the end 16A of the shift element 8A to protrude out of the bore 12A or to protrude as far as it would with a contacting operative connection.

The advantage of a noncontacting operative connection lies, in particular in the fact that the arrangement or shaping of those components which form the operative connection need not be coordinated with one another as accurately as would be necessary in the case of a contacting operative connection, so that the latter design ensures that the transfer of force will be adequate and reliable. In particular in the case of noncontacting operative connections, there is the possibility of manufacturing only one type of cleaning cassette 90 for a different cleaning or care apparatus without being obliged to accurately coordinate the area of the operative connection of the cleaning or care apparatus and the cassette 90.

In view of the many possible embodiments to which the disclosed principles may be applied, it should be recognized that the illustrated embodiments are only preferred examples and should not be taken as limiting in scope. Rather, the scope of protection is defined by the following claims. We therefore claim all that comes within the scope and spirit of these claims.

We claim:

1. A connecting device for medical or dental instruments arranged at least partially in a cleaning or care apparatus or in a cleaning cassette, the connecting device comprising:
   a plug pin for connecting an instrument,
   at least one media line for connecting a source of a cleaning or care medium to the interior of the instrument, and
   a blocking device for securing the instrument to the connecting device, so that the cleaning or care medium, which is under pressure during the cleaning or care operation, does not displace the instrument, whereby the blocking device is movable between a first position and a second position in relation to the connecting device, and in one of the two positions, the instrument can be connected to the connecting device and released from the connecting device, respectively, and in the other position the instrument is connected to the connecting device,
   wherein a direct or indirect operative connection between the blocking device and a component of the cleaning or care apparatus or between the blocking device and at least a part of the cassette is provided for transmitting to the blocking device the force required to move the blocking device from the first position into the second position.

2. The connecting device according to claim 1, wherein a non-contacting magnetic operative connection is provided in which at least parts of the blocking device and the component of the cleaning or care apparatus or the cassette are magnetic.

3. The connecting device according to claim 1, wherein a contacting operative connection is provided so that contact can be established between a component of the cleaning or care apparatus or a part of the cassette and the blocking device.

4. The connecting device according to claim 3, wherein the blocking device comprises a shift element so that the force required for the movement can be transmitted to the shift element by way of the operative connection.

5. The connecting device according to claim 4, wherein the shift element is designed as a pin or as a piston which is preferably prestressed by a spring element.

6. The connecting device according to claim 4, wherein the shift element comprises an inclined plane or a recess.

7. The connecting device according to claim 1, wherein the blocking device comprises a blocking element which is arranged so that it is radially displaceable or deformable on the plug pin.

8. The connecting device according to claim 7, wherein the blocking element comprises a spring ring.

9. The connecting device according to claim 7, wherein the blocking element comprises a protrusion.

10. The connecting device according to claim 7, wherein the blocking element comprises an elastically deformable element.

11. The connecting device according to claim 1, wherein the connecting device is designed to be rotatable.

12. The connecting device according to claim 1, wherein the connecting device is arranged in a cleaning cassette with a rotatable cover, and the cover comprises an engaging element so that at least a portion of the rotational movement of the cover can be transferred to the connecting device to move the blocking device from the first position into the second position.

13. The connecting device according to claim 12, wherein the connecting device and the cover have a shared axis of rotation which is preferably formed by a single shaft.

* * * * *